United States Patent [19]

White et al.

[11] 4,004,550

[45] Jan. 25, 1977

[54] APPARATUS FOR PREPARING MICROSCOPE SLIDES

[76] Inventors: Ronald D. White, 6466 Saipan St., Cypress, Calif. 90630; John F. Gibson, 543 Cerritos Ave., Long Beach, Calif. 90802

[22] Filed: Apr. 4, 1975

[21] Appl. No.: 565,149

Related U.S. Application Data

[63] Continuation of Ser. No. 419,947, Nov. 29, 1973, abandoned.

[52] U.S. Cl. ............................... 118/314; 118/56; 118/319
[51] Int. Cl.² .................... B05C 11/10; B05C 5/00
[58] Field of Search ............ 118/6, 7, 56, 320, 319, 118/314, 301, 52; 134/140, 153

[56] References Cited
UNITED STATES PATENTS

| | | | |
|---|---|---|---|
| 2,078,104 | 4/1937 | Stanley | 134/140 |
| 2,833,241 | 5/1958 | Crowley et al. | 118/320 X |
| 3,352,280 | 11/1967 | Hughes et al. | 118/319 X |
| 3,727,620 | 4/1973 | Orr | 134/140 X |
| 3,730,191 | 5/1973 | Doornbos | 118/301 X |

Primary Examiner—John P. McIntosh
Attorney, Agent, or Firm—Poms, Smith, Lande & Glenny

[57] ABSTRACT

A plurality of glass slides having specimens such as blood smears disposed thereon are prepared for microscopic viewing by an apparatus which automatically applies preparation solutions to the slides such as stains and buffers and thereafter automatically drys the completed slides. The staining and buffering solutions are deposited evenly over the surfaces of the slides carrying the specimens by a timed operation of one or more electromechanically actuated aerosol dispensers which produce fine sprays of the desired preparation solutions. Simultaneously with the generated spray, the plurality of slides are rotated at a relatively slow rate to cause a uniform distribution of the spray particles on the slide surfaces. Following the staining and buffering mode, an automatic drying mode is initiated in which the plurality of slides are rotated at a relatively higher speed for a timed interval after which the apparatus automatically turns off and the completed slides may be removed from the apparatus.

5 Claims, 5 Drawing Figures

APPARATUS FOR PREPARING MICROSCOPE SLIDES

This application is a continuation of application Ser. No. 419,947, filed Nov. 29, 1973, now abandoned.

BACKGROUND OF THE INVENTION

The present invention generally relates to apparatus for preparing specimens on glass slides suitable for viewing under high magnification such as by a microscope.

Although the present invention has general utility in preparing all types of microscope slides and slide specimens, there is a particular need for a more automatic and efficient process for preparing biological or medical specimens for diagnosing and treating medical conditions. To a large extent modern medical practice depends upon the laboratory tests which may be conducted on specimens obtained from the patient.

The analysis of blood samples from the patient is an extremely valuable tool. Usually the blood specimens are analyzed by preparing blood smears on microscopic slides and subjecting the blood smear specimen to microscopic viewing. For this purpose in order to prepare a blood smear for lab testing, fresh whole blood is smeared on to a standard laboratory glass slide and thereafter a staining solution is applied to the smear in order to bring out or enhance the viewability thereof. Following the staining operation, a separate process is performed to apply a buffering solution which fixes or stabilizes the stained specimen so that it remains in a relatively permanent state during the microscopic analysis. Still another operation must be performed after the buffering, and that is to place the slides in an oven or the like to evaporate any remaining liquid and thus to dry the blood smear, stain solution and buffering solution. This completes the preparation process.

Although in small laboratories where only a few slides are prepared at a time, the foregoing individual operations may not be too disadvantageous. However in much larger laboratories for example those associated with a large metropolitan hospital, the foregoing technic of preparing slides is wholly inefficient, occupying too much of the laboratory technician's time and tending to produce nonuniformity in the prepared slides. Additionally, the increased handling of the glass slides typically necessitated by the various individual processing steps, leads to more accidental breakage of the glass slides and loss of specimens.

SUMMARY OF THE INVENTION

In general, it is an object of the present invention to overcome the foregoing disadvantages associated with conventional processing of specimen slides. There have been previous attempts to automate the slide preparation such as exemplified by U.S. Pat. No. 3,352,280 issued to R. Hughes et al.

However, this and other heretofore proposed apparatus have not met with wide acceptance. It is believed that the reason for this lies in the complexity, expense, susceptibility to malfunction, and in general the inability of these previous machines to accomplish the underlying objective, that is to more efficiently and more economically prepare specimen slides. For example, the apparatus disclosed in U.S. Pat. No. 3,352,280 attempts to apply the stain and buffering solution by dribbling it in liquid form on to a rapidly rotating surface adjacent the individual specimen slides. The rapidity of rotation of the slides is said to force the stain and buffering solution outwardly under centrifugal force to apply layers of these liquids to the slide specimens. However, it is not believed that such an apparatus is capable of producing suitably uniform staining and buffering.

The method and apparatus according to the present invention overcomes these and other shortcomings of the prior art as will become apparent to those skilled in the art from a consideration of the following detailed description and appended drawings of a few particular embodiments thereof.

IN THE DRAWINGS

DESCRIPTION OF PREFERRED EMBODIMENTS

Figure 1:
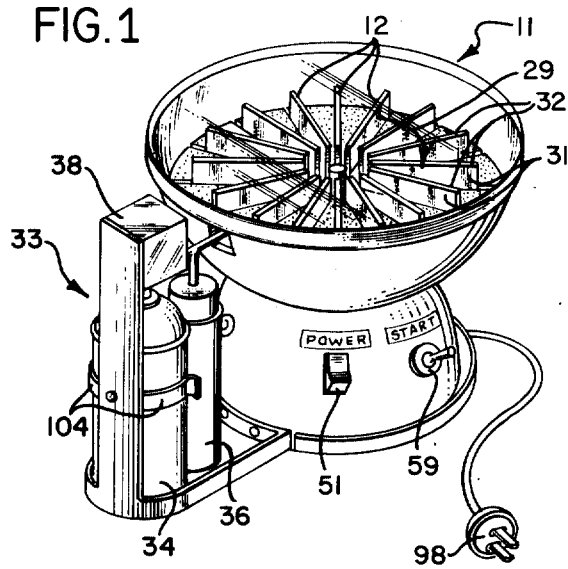
FIG. 1 is an overall perspective view of the apparatus for automatically preparing slides in accordance with the present invention.
Figure 2:
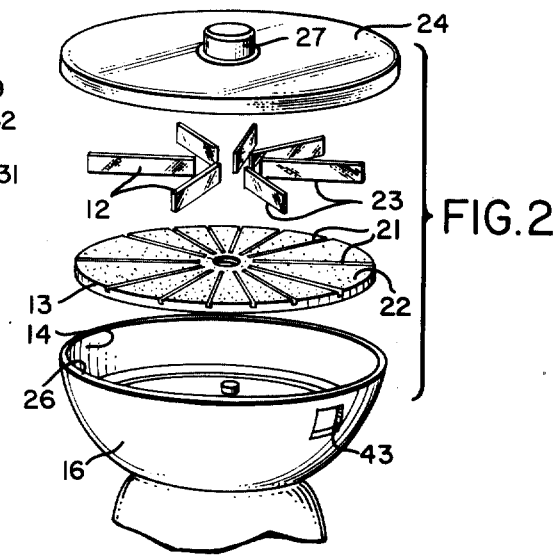
FIG. 2 is an assembly view also in perspective showing some of the principal components of the apparatus of FIG. 1.

With reference to FIGS. 1 through 4, the present invention provides a method and apparatus for automatically preparing microscope specimen slides. More particularly, an apparatus indicated at 11 serves to receive a plurality of specimen slides 12, which may be of a standard rectangular shape glass construction and on which a specimen or other sample has been deposited.

For the particular embodiments disclosed herein, slides 12 are described as receiving a blood smear specimen, and the solutions automatically applied by apparatus 11 are intended for this particular type of specimen. It will be apparent however, that the present invention may be used for a variety of different slide specimens and the solutions applied for staining, buffering or other purpose may vary depending upon the requirements of the particular specimen.

Apparatus 11 is constructed to include a rotatable slide carrier means for receiving and holding a plurality of the specimen slides 12. In this instance, the carrier means is provided by a turntable 13 mounted for rotation inside a bowl shaped chamber 14 defined by a bowl structure 16.

Turntable 13 is rotatably driven by an electrical motor drive means, here provided by a motor 17 having a vertically oriented drive shaft 18 connected to an overlying turntable hub 19.

Turntable 13 is formed or provided with a plurality of slide holder means for receiving and removably holding a corresponding plurality of the specimen slides 12. In this instance, the slide holder means are provided by a plurality of radially extending slots or recesses 21 formed in an upper face 22 of turntable 13 for receiving a lower edge 23 of each of slides 12 when disposed with their longitudinal axes in the horizontal plane and thus parallel to surface 22.

By mounting slots 21 along the radii like the spokes of a wheel, the number of slides 12 which may be accommodated by apparatus 11 is maximized for greatest efficiency. Furthermore, as more fully disclosed herein, this orients the faces of slides 12 advantageously for receiving the applied preparation solutions.

To retain the preparation solutions within the apparatus during operation thereof and moreover to provide a generally enclosed chamber 14 within which the slides are rotated, a closure or lid 24 may be provided mating with an upper peripheral edge 26 of bowl shaped structure 16 as illustrated. If desired, lid 24 may be of a transparent material to permit viewing of the slides 12 during preparation.

Apparatus 11 further includes one or more controllable spray dispenser means for injecting a mist or spray 28 of slide preparation solution toward or in the proximity of plurality of rotating slides 12. The spray 28 which is developed in this manner intercepts the slides 12 which are simultaneously rotated by turntable 13 causing the solution to be uniformly deposited on the surfaces of the slide. Preferably, turntable 13 is rotated in a direction with the side of each slide 12 having the specimen thereon leading the nonspecimen or nonprepared slide surface. For example in this case with turntable 13 rotating in a direction indicated by arrow 29, the specimens would be placed on the leading surfaces or sides 31 rather than on the trailing surfaces 32 so that the specimen sides 31 intercept the spray 28 causing most of the spray particles to be deposited on the desired surface.

More particularly, the spray dispenser means is preferably provided by an aerosol spray assembly 33 which includes both an aerosol propellant and a slide preparation solution. In this particular embodiment, a separate and controllable aerosol propellant can 34 is provided in combination with a separate solution container 36, both of which are connected by conduit means 37 to develop a solution spray 28 of the contents of container 36. Thus, aerosol propellant can 34 which merely serves to provide a source of propellant gas, and solution container 36 together with conduit means 37 provide the spray assembly 33.

Spray assembly 33 is automatically rendered operable at the proper time and for the proper duration by an electrically operated spray actuator means. In this instance, the actuator means is provided by an electromagnetic solenoid assembly 38 having a plunger 39 selectively driven to engage and depress an actuator valve 41 of aerosol can 34. Actuator valve 41 may be of a standard type in which a downward force thereon releases the propellant from can 34 and allows it to escape under pressure into conduit means 37.

Conduit means 37 includes a first conduit section 42 which may be extended into chamber 14 through an aperture or window 43 of structure 16 as illustrated, and a second conduit section 43 which joins section 42 at an aspirating or suctioning junction 44 serving to aspirate the liquid contents of container 36 into the stream of gas flowing toward chamber 14 through conduit section 42. The arrangement of propellant can 34, conduit means 37 and container 36 are known per se and constitute only one form of the spray assembly 33 which may be employed in the present invention.

In the presently disclosed embodiment, the preparation solution provided in container 36 includes both a staining solution and a buffering solution for preparing blood specimens. By this arrangement, the staining and buffering or fixing of the slides 12 is accomplished by the same spray 28 and solenoid 38 may be operated just once during an apparatus cycle.

On the other hand, one or more preparation solutions may be provided directly within an aerosol can 34 of the type including both the applied solution and the aerosol propellant in a well-known manner. It has been found, however, that certain solutions if provided within the aerosol can 34 tend to freeze under the evaporating effect of the aerosol liquid propellant, and in such case it is possible to provide the solution in a separate container such as the here illustrated container 36.

Figure 3:
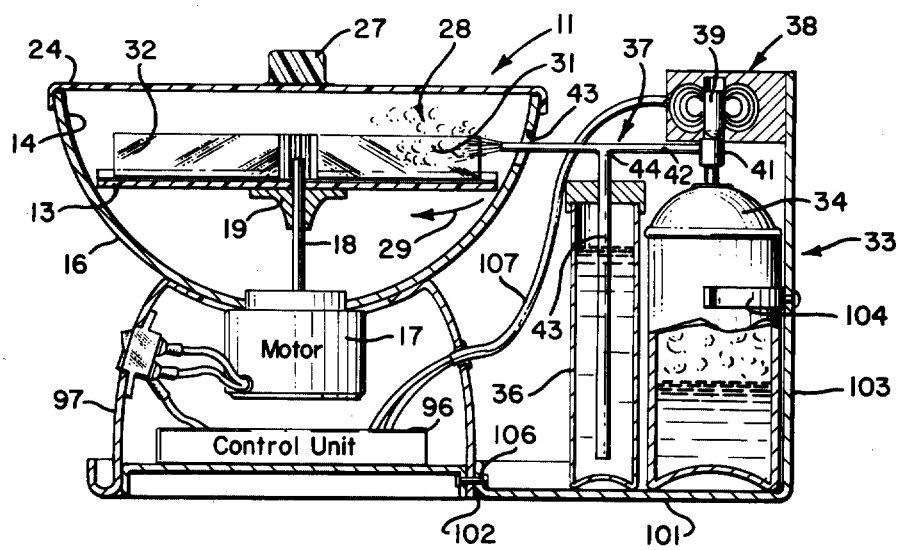
FIG. 3 is a vertical cross-sectional view taken generally along a center plane of the apparatus shown in FIG. 1.
Figure 4:
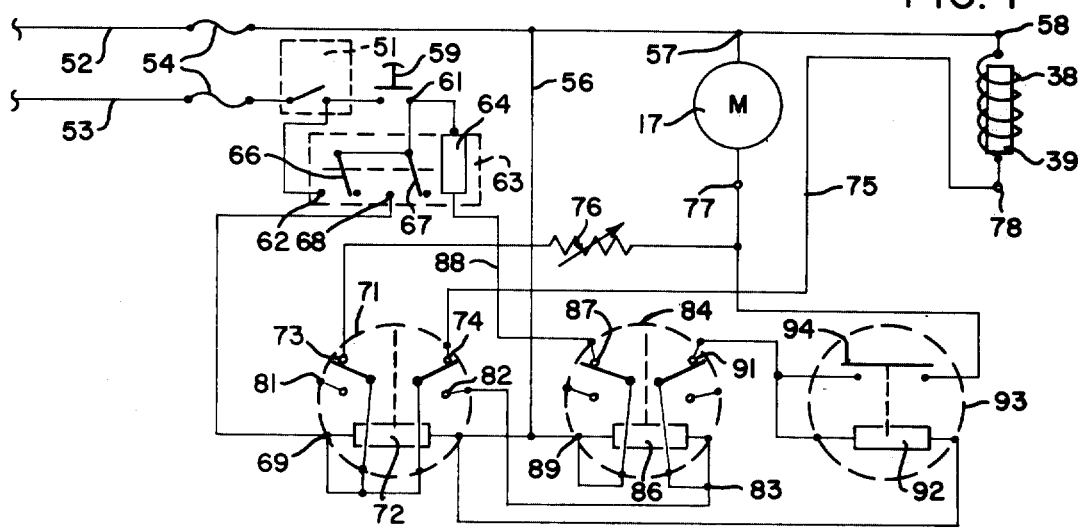
FIG. 4 is a detailed schematic diagram of the control circuitry employed in the apparatus of FIGS. 1 through 3.
Figure 5:
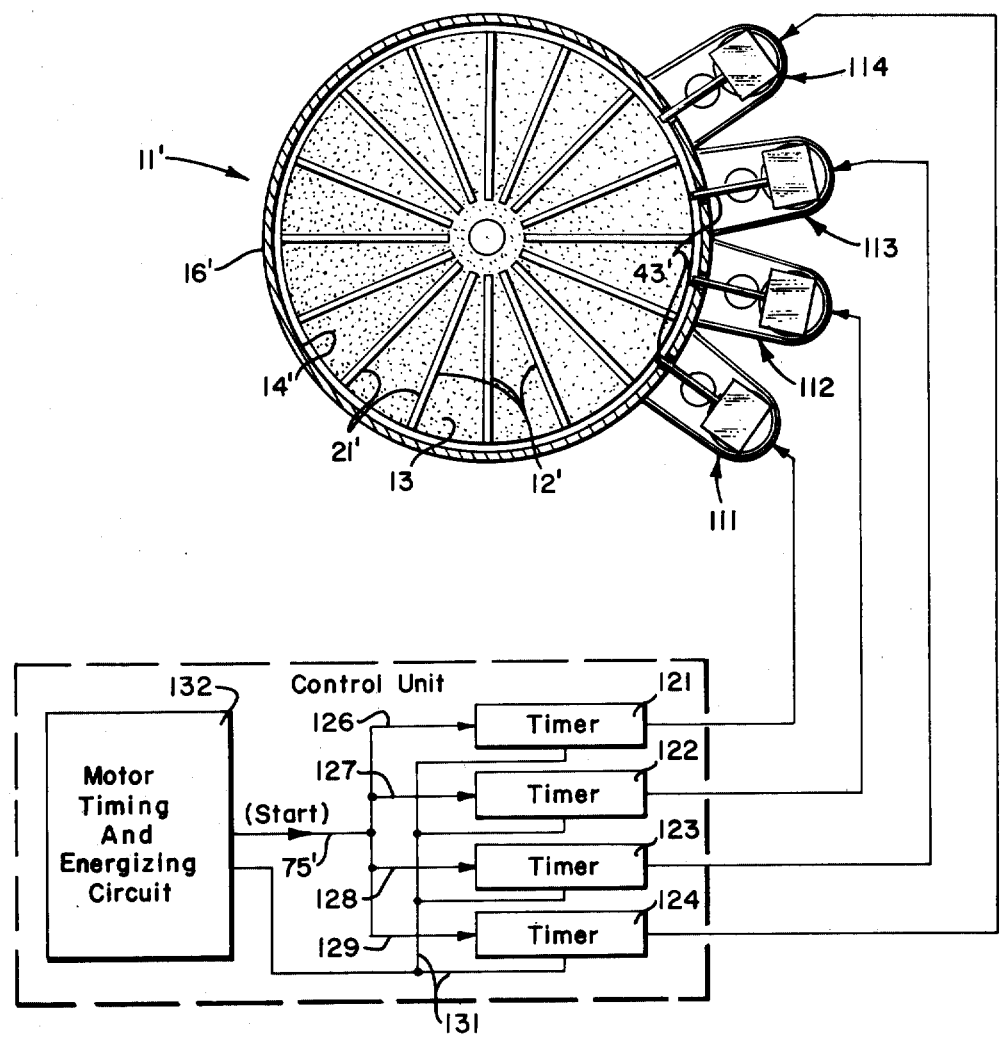
FIG. 5 is a schematic representation of an alternative embodiment of the present invention.

Also, in the embodiment of FIGS. 1 through 4, the stain and buffering solutions are applied simultaneously in a single spray, whereas these or other preparation solutions may be applied separately and sequentially by an alternative embodiment of the present invention to be described more fully herein in connection with FIG. 5.

To coordinate the functions of apparatus 11 an electrical control means is provided including timing means connected to the motor drive means provided by motor 17 and connected to the spray actuator means provided by solenoid 38. This timing means serves to provide a timed spraying interval in which the motor 17 and solenoid 38 are jointly energized and thereafter a timed rotating interval in which only the motor drive means in the form of motor 17 is energized. More particularly, the control means including the timing means provides for simultaneously driving motor 17 and energizing solenoid 38 in a spray dispensing mode at the termination of which only motor 17 is energized during a drying mode. Moreover, during the spray mode, motor 17 is energized at a relatively slow rate of rotation such that turntable 13 and the slides 12 carried thereby are moved at an optimum rate for intercepting the solution spray 28 to receive a uniform deposit thereof on the specimen side 31 of the slides. However, after the spray dispensing mode has terminated and solenoid 38 is de-energized to terminate the aerosol spray, then a drying mode is entered into in which motor 17 is energized at a substantially greater rate of rotation.

Although the exact speeds of rotation of motor 17 and turntable 13 during the spray and drying modes is not believed critical, a speed of around of 40 rpm for the spraying mode and a speed of around 200 rpm for the drying mode has been found satisfactory. The relatively lower rate of rotation during the spraying mode is desirably fast enough to provide uniform deposition of the spray solution and yet slow enough to prevent the spray from being blown out of contact with surfaces 31 of the slides. The drying speed on the other hand should develop sufficient air currents to speed the evaporation and drying process. Typically, the spraying speed will be adjusted to an optimum level in the above-indicated range and the drying speed will be approximately 3 to 7 times greater than the spraying mode speed.

Finally, the control means of the present invention provides for automatically shutting off the apparatus after a timed interval of the drying mode. This restores the apparatus to an initial state, with the turntable 13 stopped so that lid 24 may be opened and the fully prepared slides withdrawn from the apparatus.

Although the circuitry for the control means may take many different forms, in this particular instance, the disclosed apparatus utilizes the control circuit shown in FIG. 4. In conjunction with the circuit of FIG. 4, a manually operated power switch 51 may be provided as illustrated in FIGS. 1 and 4 for selectively applying or interrupting a line voltage to the apparatus available over lines 52 and 53, each of which may be provided with a fuse 54. Line 53 is connected directly to a control line 56, one terminal 57 of motor 17 and one terminal 58 of solenoid 38 as illustrated.

The other line 53 is connected through power switch 51 as illustrated in FIG. 4 to a push-button start switch 59, which may be mounted along with switch 51 on apparatus 11, to a contact 61. Also, switch 51 connects line 53 to a relay contact 62 of a relay 63. Relay 63 is illustrated in an unenergized condition and may be latched to an energized condition by momentarily operating switch 59 to energize a relay coil 64 connected to switch contact 61 with the circuit to the opposite end of coil 64 being completed through a set of relay contacts to control line 56 connected to line 52. Once energized, relay 63 is latched to the energized state through contact 66 and 62 connecting line 53 to contact 61 and thus to one side of relay coil 64.

Simultaneously with the energization of relay 63, the normally open contacts 67 and 68 are closed thus supplying line voltage from line 53 to a junction 69 of a first relay timer 71. Relay timer 71 includes a relay coil 72 which must receive an applied voltage thereacross for a timed interval before the contacts of relay timer 71 are operated. Thus, initially upon receiving the line voltage at junction 69, relay coil 72 remains unenergized and the normally closed contacts 73 and 74 remain closed to energize motor 17 through timer contact 73, variable resistor 76 and a second terminal 77 of the motor, and to actuate solenoid 38 via contacts 74 and a second terminal 78 of the solenoid.

This condition of the circuit corresponds to the spraying mode of apparatus 11 described above in which motor 17 is energized at a relatively low rate of rotation and solenoid 38 is concurrently energized to inject the solution spray 28 into chamber 14.

After a predetermined time delay which may be adjusted by appropriate selection of relay timer 71, coil 72 is energized causing normally closed contacts 73 and 74 to open and normally open contacts 81 and 82 to close. Contacts 81 are not used in this instance, however normally open contacts 82, now closed, apply the incoming line voltage available at junction 69 to a junction 83 of a second relay timer 84. Relay timer 84 operates in a similar manner to timer 71, and a line voltage must be applied across a coil 86 thereof for a predetermined time before the contacts of timer 84 are operated.

Before coil 86 of timer 84 is operated, the normally closed contacts 87 thereof maintain relay 63 energized by connecting a line 88 through the normally closed contacts 87 to a junction 89 which in turn is extended back to connecting line 56 to the other incoming line 52 of the line voltage.

Also, timer 84 through normally closed contacts 91 energizes a coil 92 of motor drive relay 93. Relay 93 through its normally open contacts 94 applies the line voltage available at lines 52 and 53 directly across the first and second terminals 57 and 77 of motor 17 for energizing the motor at its full rotational rate. Thus during this mode, motor 17 is operated at a speed appropriate for the drying mode. Also, it is noted that relay timer 84 serves to time the drying interval.

After a predetermined elapsed time for the drying mode, relay timer 84 becomes energized via coil 86 causing normally closed contacts 87 and 91 to be opened. The opening of contacts 87 unlatches the previously latched relay 63 while the opening of contacts 91 de-energizes motor relay 93 thus shutting off motor 17. This terminates the various operating modes of the apparatus and restores the control circuitry to its original or starting condition ready to receive another start via push-button switch 59.

The control circuitry of FIG. 4 may all be mounted in a control unit 96 disposed within an annular base structure 97 serving to support bowl structure 16 and motor 17 as illustrated in FIG. 3. Switches 51 or 59 may be mounted as shown on base structure 97 for convenient manual access. A plug 98 may be provided for connecting the apparatus to a standard utility outlet for energizing lines 52 and 53.

For receiving and supporting aerosol spray assembly 33, a base extension 101 may be provided extending radially outwardly from a lower support surface 102 of base structure 97 and having an upstanding portion 103 extending upwardly adjacent assembly 33 for supporting solenoid 38 in an overlying relation to aerosol propellant can 34. Upstanding portion 103 may have a spring clip 104 mounted thereto for securement of aerosol can 34 as illustrated. Base extension 101 may be fastened to base structure 97 by suitable means as illustrated at 106, and the electrical wiring between control unit 96 and solenoid 38 may be provided by a flexible cable 107.

With reference to FIG. 5, an alternative embodiment of the present invention is illustrated in which a plurality of control spray dispenser means are mounted adjacent the periphery of a rotating slide carrier means. In this instance, the plurality of spray means may be constructed similar to spray assembly 33 and solenoid 38 and mounted at a plurality of circumferentially spaced spray stations such as indicated at 111, 112, 113 and 114. Each of these stations may be constructed similarly to the single spray station of assembly 33 and solenoid 38 shown in FIGS. 1 through 4.

To inject the plurality of sprays into a chamber 14' of bowl structure 16' as shown in FIG. 5, there are a plurality of spray apertures or windows 43', one for each spray station. Other than these modifications, the apparatus of FIG. 5 may be similar to that shown in FIGS. 1 through 3, in that a turntable 13' is provided with a plurality of radial slots 21' for accommodating the corresponding plurality of specimen slides 12'.

It is an advantage of this embodiment that two or more spray stations similar stations 111–114 may be provided for applying different preparation solutions either concurrently or according to a preprogrammed sequence. For example if desired, two such spray stations may be provided, one for introducing a stain spray while a second station is provided for injecting the buffering solution. If the plurality of spray stations 111–114 are formed similar to the embodiment of FIGS. 1 through 3, each will be provided with a separate solution container similar to container 36 of FIGS. 1 through 3, for storing and dispensing a different solution or mixture of solutions.

Each of the individual spray stations 111–114 may be provided with a different timing means as part of the electrical control means, such as the here illustrated timers 121, 122, 123 and 124 for selectively energizing the solenoid actuators associated with stations 111–114, respectively. That is each of timers 121–124 may, if desired, individually control the time interval during which the associated spray assembly is actuated.

With reference to the overall control circuit shown in FIG. 4, the various timers 121–124 may be triggered or started from a control line 74 available from the normally closed contacts 74 of relay timer 71. That is each of the separate inputs 126, 127, 128 and 129 may be jointly connected to a control line 74' corresponding to lines 75 of FIG. 4. In the case of the embodiment of FIG. 5, the control line 75' originating from the normally closed contacts 74 of relay timer 71 would not be extended directly to and for controlling a solenoid as it is in the embodiment of FIG. 4. Rather, control line 75' is extended jointly to the inputs 126–129 of timers 121–124 for controlling the associated actuator solenoids only through the respective timers. A return path may be provided for the timer circuits as indicated by return line 131 connected back to motor timing and energizing circuit 132 which would correspond substantially to the circuit in FIG. 4 except for the deletion of solenoid 38. In other words, the two connecting lines of FIG. 4 extended to and for driving the solenoid 38 may instead provide the output lines 75' and 132 for activating the various timer circuits. Of course, this is only one possible arrangement for the timing of spray stations 111–114, and many suitable alternative arrangements for the timer circuitry will occur to those skilled in the art. This particular arrangement allows the overlapping or concurrent operation of the sprays associated with the various stations. For example, station 111 may provide a solution spray which is timed by timer 121 and which lasts for the full duration of the spray mode, while stations 112–114 may occur for brief intervals during the spray mode and thus have a short concurrent period with the spray from station 111.

In general, it will be seen that any number of different spray modes and combinations thereof may be provided by the embodiment of FIG. 5. Thus, microscope slides which would otherwise involve a considerable number of separate steps during the preparation thereof, are quickly and efficiently prepared by this embodiment of the invention.

As can perhaps best be seen from FIGS. 1, 3 and 5, taken together, the spray nozzle 43 or 43' lies in a plane which is substantially parallel to the upper face of support surface 22 of the carrier or turntable 13 and the path of the spray which lies in that plane is located within the lateral confines of the slide which intercepts the spray so that, referring to the exemplary embodiment shown in FIG. 3, a straight line extension of nozzle 43 will lie within the lateral (upper and lower) edges of the slide. Moreover, as can best be visualized with respect to FIG. 5, the nozzle (43') forms a time varying acute angle with the slide which intercepts the spray therefrom, this angle changing during the rotation of the slide so that the spray moves across the face (leading surface) of the slide.

While only a limited number of embodiments of the present invention have been disclosed herein, it will be readily apparent to persons skilled in the art that numerous changes and modifications may be made thereto without departing from the spirit of the invention. Accordingly, the foregoing disclosure and description thereof are for illustrative purposes only and do not in anyway limit the invention which is defined only by the following claims.

We claim:

1. An apparatus for automatically preparing microscope slides having blood smear specimens or the like on a face thereof comprising:

a base;

rotatable slide carrier means rotatably mounted on an axis on said base and including a planar support surface substantially perpendicular to said axis and having a plurality of slide holder means thereon for receiving and removably holding a corresponding plurality of specimen slides in which the faces thereof are substantially perpendicular to the planar support surface;

electrical motor drive means for rotating said carrier means relative to said base;

spray means disposed adjacent said rotating carrier means and stationary with respect to said base for producing an atomized spray of a slide preparation solution in the proximity of the rotating slides to cause the atomized solution to be deposited on the faces of the slides over the specimen when the slide is brought into register with the spray means, said spray means including a spray nozzle having a spray axis positioned relative to said carrier means such that the nozzle axis lies in a plane substantially parallel to the plane of the support surface and that the portion of the spray pattern produced by the nozzle which lies within the parallel plane of the nozzle is located within the lateral confines of the slide which intercepts the spray pattern, said nozzle forming a time varying acute angle with the slide brought into register therewith so that said spray moves across the face of the slide during the movement of the latter;

electrically operated spray actuator means associated with said spray means for selective actuation thereof to produce said spray; and electrical control means including a timing means connected to said motor drive means and to said spray actuator means for selective timed energization thereof including a timed spray mode in which said motor drive means and said spray actuator means are jointly energized and a timed drying mode in which only said motor drive means is energized.

2. The apparatus of claim 1, said electrical control means being further defined as including pushbutton start means for manually initiating said spray mode and including means for automatically de-energizing said motor drive means after said timed drying mode, whereby the apparatus is automatically restored to its initial condition in which both said motor drive means and said spray actuator means are de-energized at the end of said drying mode.

3. The apparatus of claim 1, said slide holder means on said turntable comprising a plurality of elongated slots extending along the radii of said turntable for receiving a lower elongated edge of each of said plurality of slides.

4. The apparatus of claim 1, said spray means comprising a plurality of spray dispenser stations each including a spray dispensing means and an actuator means for selective operation of an associated spray dispenser means, and said electrical control means including timing means for operating said plurality of actuator means at predetermined times during said spray mode, whereby a plurality of different slide preparation solutions may be applied to the specimen slides.

5. The apparatus of claim 1, said spray means including an aerosol spray propellant container and said actuator means cooperating with said container to selectively release said aerosol propellant therefrom to generate said aerosol solution spray.

* * * * *